US012702638B2

(12) United States Patent
Farmer et al.

(10) Patent No.: US 12,702,638 B2

(45) **Date of Patent: *Aug. 11, 2026**

(54) COSMETIC COMPOSITIONS FOR SKIN HEALTH AND METHODS OF USING SAME

(71) Applicant: Locus Solutions IPCo, LLC, Solon, OH (US)

(72) Inventors: Sean Farmer, Ft. Lauderdale, FL (US); Ken Alibek, Solon, OH (US)

(73) Assignee: LOCUS SOLUTIONS IPCO, LLC, Solon, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/833,304

(22) Filed: Jun. 6, 2022

(65) Prior Publication Data

US 2022/0304920 A1 Sep. 29, 2022

Related U.S. Application Data

(63) Continuation of application No. 16/609,346, filed as application No. PCT/US2018/030229 on Apr. 30, 2018, now Pat. No. 11,446,235.

(60) Provisional application No. 62/502,714, filed on May 7, 2017, provisional application No. 62/537,057, filed on Jul. 26, 2017.

(51) Int. Cl.

| | |
|---|---|
| ***A61K 8/99*** | (2017.01) |
| ***A61K 8/34*** | (2006.01) |
| ***A61K 8/60*** | (2006.01) |
| ***A61K 8/64*** | (2006.01) |
| ***A61K 8/66*** | (2006.01) |
| ***A61K 8/73*** | (2006.01) |
| ***A61K 8/81*** | (2006.01) |
| ***A61K 8/9794*** | (2017.01) |
| ***A61K 9/00*** | (2006.01) |
| ***A61K 9/06*** | (2006.01) |
| ***A61K 9/08*** | (2006.01) |
| ***A61K 9/10*** | (2006.01) |
| ***A61K 9/107*** | (2006.01) |
| ***A61K 9/12*** | (2006.01) |
| ***A61K 31/05*** | (2006.01) |
| ***A61K 31/728*** | (2006.01) |
| ***A61K 38/47*** | (2006.01) |
| ***A61K 47/32*** | (2006.01) |
| ***A61P 17/02*** | (2006.01) |
| ***A61P 17/10*** | (2006.01) |
| ***A61P 17/12*** | (2006.01) |
| ***A61Q 5/00*** | (2006.01) |
| ***A61Q 15/00*** | (2006.01) |
| ***A61Q 17/00*** | (2006.01) |
| ***A61Q 19/00*** | (2006.01) |
| ***A61Q 19/02*** | (2006.01) |
| ***A61Q 19/08*** | (2006.01) |

(52) U.S. Cl.

CPC ................ *A61K 8/99* (2013.01); *A61K 8/347* (2013.01); *A61K 8/60* (2013.01); *A61K 8/602* (2013.01); *A61K 8/64* (2013.01); *A61K 8/66* (2013.01); *A61K 8/735* (2013.01); *A61K 8/8147* (2013.01); *A61K 8/9794* (2017.08); *A61K 9/0014* (2013.01); *A61K 9/06* (2013.01); *A61K 9/08* (2013.01); *A61K 9/10* (2013.01); *A61K 9/107* (2013.01); *A61K 9/12* (2013.01); *A61K 31/05* (2013.01); *A61K 31/728* (2013.01); *A61K 38/47* (2013.01); *A61K 47/32* (2013.01); *A61P 17/02* (2018.01); *A61P 17/10* (2018.01); *A61P 17/12* (2018.01); *A61Q 5/00* (2013.01); *A61Q 15/00* (2013.01); *A61Q 17/00* (2013.01); *A61Q 19/00* (2013.01); *A61Q 19/007* (2013.01); *A61Q 19/008* (2013.01); *A61Q 19/02* (2013.01); *A61Q 19/08* (2013.01)

(58) Field of Classification Search

None

See application file for complete search history.

(56) References Cited

U.S. PATENT DOCUMENTS

| | | | |
|---|---|---|---|
| 4,902,512 | A | 2/1990 | Ishigami et al. |
| 5,756,471 | A | 5/1998 | Hillion et al. |
| 5,981,497 | A | 11/1999 | Maingault |
| 6,057,302 | A | 5/2000 | Borzeix |
| 6,403,108 | B1 | 6/2002 | Abdullah |
| 6,509,021 | B1 | 1/2003 | Weiss et al. |
| 10,065,982 | B2 | 9/2018 | Hirata et al. |

(Continued)

FOREIGN PATENT DOCUMENTS

| | | | |
|---|---|---|---|
| CN | 102078282 | A | 6/2011 |
| CN | 103800224 | A | 5/2014 |

(Continued)

OTHER PUBLICATIONS

English translation for KR10-2011-0012699 A (Year: 2011).*

(Continued)

*Primary Examiner* — Sin J Lee

(74) *Attorney, Agent, or Firm* — BENESCH, FRIEDLANDER, COPLAN & ARONOFF

(57) ABSTRACT

The topical cosmetic compositions and methods of the subject invention can be used to treat and/or prevent a variety of skin conditions, including, for example, age spots, acne, scars, body odor, aging-related conditions (e.g., wrinkles, looseness and dryness), and scalp issues (e.g., dandruff, seborrheic dermatitis and hair loss). In preferred embodiments, the compositions according to the subject invention comprise biological amphiphilic molecules produced by microorganisms.

4 Claims, 1 Drawing Sheet

(56) References Cited

U.S. PATENT DOCUMENTS

| | | | | |
|---|---|---|---|---|
| 2003/0050277 | A1 | 3/2003 | Kajimoto et al. | |
| 2008/0187593 | A1* | 8/2008 | Bluth | A61K 9/0014 514/23 |
| 2008/0311234 | A1 | 12/2008 | Yoneda et al. | |
| 2009/0029879 | A1 | 1/2009 | Soni et al. | |
| 2009/0203649 | A1 | 8/2009 | Kato et al. | |
| 2010/0004472 | A1 | 1/2010 | Kitagawa et al. | |
| 2010/0143316 | A1 | 6/2010 | Hsieh et al. | |
| 2010/0168405 | A1* | 7/2010 | Suzuki | A61Q 19/08 536/4.1 |
| 2010/0267684 | A1 | 10/2010 | Seong et al. | |
| 2011/0044972 | A1 | 2/2011 | Fieldhouse et al. | |
| 2011/0257116 | A1* | 10/2011 | Kitagawa | A61Q 19/008 514/25 |
| 2012/0039853 | A1 | 2/2012 | Corveleyn et al. | |
| 2013/0324406 | A1 | 12/2013 | Chisholm et al. | |
| 2013/0331466 | A1 | 12/2013 | Gross et al. | |
| 2014/0127257 | A1 | 5/2014 | Schiemann et al. | |
| 2014/0296168 | A1 | 10/2014 | Schilling et al. | |
| 2014/0323757 | A1 | 10/2014 | Kim | |
| 2014/0364381 | A1 | 12/2014 | Ju et al. | |
| 2015/0037302 | A1 | 2/2015 | Bralkowski et al. | |
| 2015/0044317 | A1* | 2/2015 | Farmer | A61K 8/9728 424/780 |
| 2015/0045290 | A1* | 2/2015 | Coutte | A61P 31/10 530/321 |
| 2016/0083757 | A1 | 3/2016 | Fonesca et al. | |
| 2016/0199530 | A1 | 7/2016 | Ploger et al. | |
| 2016/0213757 | A1 | 7/2016 | Edelson et al. | |
| 2016/0235661 | A1 | 8/2016 | Changoer et al. | |
| 2016/0324747 | A1 | 11/2016 | Ito et al. | |
| 2016/0375071 | A1 | 12/2016 | Figueroa et al. | |
| 2017/0071842 | A1 | 3/2017 | Schelges et al. | |
| 2017/0119638 | A1 | 5/2017 | Kondo et al. | |
| 2018/0264051 | A1 | 9/2018 | Prabhune et al. | |
| 2019/0231668 | A1 | 8/2019 | Yoo et al. | |
| 2019/0307788 | A1 | 10/2019 | Wakayama | |

FOREIGN PATENT DOCUMENTS

| | | | |
|---|---|---|---|
| CN | 104232528 | A * | 12/2014 |
| EP | 0540074 | A1 | 5/1993 |
| EP | 1228752 | A2 | 8/2002 |
| EP | 1964546 | A1 | 9/2008 |
| EP | 2931237 | B1 | 4/2018 |
| JP | H10501260 | A | 2/1998 |
| JP | 11512092 | A | 10/1999 |
| JP | 2003113040 | A | 4/2003 |
| JP | 2005306863 | A | 11/2005 |
| JP | 2008044855 | A | 2/2008 |
| JP | 2009029788 | A | 2/2009 |
| JP | 2009149566 | A | 7/2009 |
| KR | 20110012699 | A | 2/2011 |
| KR | 10-1485896 | B1 * | 1/2015 |
| WO | 2004020647 | A1 | 3/2004 |
| WO | 2007060956 | A1 | 5/2007 |
| WO | 2011127101 | A1 | 10/2011 |
| WO | 2012010407 | A1 | 1/2012 |
| WO | 2013092421 | A1 | 6/2013 |
| WO | 2014095367 | A1 | 6/2014 |
| WO | 2015034007 | A1 | 3/2015 |
| WO | 2015153476 | A1 | 10/2015 |
| WO | 2017044953 | A1 | 3/2017 |
| WO | 2017051433 | A1 | 3/2017 |
| WO | 2018049182 | A2 | 3/2018 |
| WO | 2018129299 | A1 | 7/2018 |
| WO | 2019022997 | A1 | 1/2019 |

OTHER PUBLICATIONS

Ishii et al (abstract for “Transdermal administration of lactoferrin with sophorolipid”, Biochemistry and Cell Biology, vol. 90 (3) (2012), p. 504-512) (Year: 2012).*

Morita et al (“Mannosylerythritol Lipids: Production and Applications”, Journal of Oleo Science, vol. 64(2), p. 133-141 (2015)) (Year: 2015).*

English translation for KR10-1485896 B1 (2015).*

English translation for CN 104232528A (Year: 2014).*

De Brito, D., Biosurfactants from renewable raw materials, Universidade do Minho Departamento de Engenharia Biologica, Nov. 2013, pp. 1-93.

De Oliveira, M., et al., “Review: Sophorolipids A Promising Biosurfactant and it's Applications.” International Journal of Advanced Biotechnology and Research, 2015, 6(2): pp. 161-174.

Gharaei-Fathabad, E., “Biosurfactants in Pharmaceutical Industry (A Mini-Review).” American Journal of Drug Discovery and Development, 2010, 1(1): pp. 58-69.

Kurtzman, C.P., et al., “Production of sophorolipid biosurfactants by multiple species of the Starmerella (Candida) bombicolayeast clade.” FEMS Microbiol Lett, 2010, 311: pp. 140-146.

Nitschke, M., et al., “Production and properties of a surfactant obtained from Bacillus subtilis grown on cassava wastewater.” Bioresource Technology, 2006, 97: pp. 336-341.

Santos, D.K.F., et al., “Biosurfactants: Multifunctional Biomolecules of the 21st Century.” International Journal of Molecular Sciences, 2016, 17(401): pp. 1-31.

Sen, R., “Biosurfactants: Advances in Experimental Medicine and Biology.” Landes Bioscience and Springer Science +Business Media, LLC, 2010, 672: pp. 1-331.

Sharma, A. et al., “A study on biosurfactant production in Lactobacillus and *Bacillus* sp.” Int. J. Curr. Microbiol. App. Sci., 2014, 3(11): pp. 723-733.

Shen, C., et al., “Targeted killing of myofibroblasts by biosurfactant di-rhamnolipid suggests a therapy against scar formation.” Scientific Reports, 2016, 6: 37553, pp. 1-10.

Silva, R., et al., “Applications of Biosurfactants in the Petroleum Industry and the Remediation of Oil Spills.” International Journal of Molecular Sciences, 2014, 15: pp. 12523-12542.

Takahashi, M., et al., “Production of Sophorolipid Glycolipid Biosurfactants from Sugarcane Molasses Using Starmerella bombicola NBRC 10243.” Journal of Oleo Science, 2011, 60(5): pp. 267-273.

Torres Faria, N., et al., “Production of glycolipid biosurfactants, mannosylerythritol lipids, from pentoses and D-glucose/D-xylose mixtures by *Pseudozyma* yeast strains.” Process Biochemistry, 2014, 49(11): pp. 1790-1799.

Bhadoriya, S.S., et al., “Biosurfactants: A New Pharmaceutical Additive for Solubility Enhancement and Pharmaceutical Development.” Biochem Pharmacol, 2013, 2(2): 1000113, pp. 1-5.

Imura, T., et al., “Spontaneous Vesicle Formation from Sodium Salt of Acidic Sophorolipid and Its Application as a Skin Penetration Enhancer.” Journal of Oleo Science, 2014, 63(2): 141-147.

Ines, M., et al., “Glycolipids biosurfactants; Potential related Biomedical and Biotechnical Applications.” Carbohydrate Research, 2015, 416: 59-69.

Kim, K., et al. “Characteristics of Sophorolipid as an Antimicrobial Agent.” J. Microbiol. Biotechnol., 2002, 12(2): 235-241.

Kitamoto, D., et al., “Self-assembling properties of glycolipid biosurfactants and their potential applications.” Current Opinion in Colloid & Interface Science, 2009, 14: 315-328.

Office Action issued in Canadian Patent Application No. 3,062,432, dated Jun. 17, 2025.

* cited by examiner

COSMETIC COMPOSITIONS FOR SKIN HEALTH AND METHODS OF USING SAME

CROSS-REFERENCE TO RELATED APPLICATIONS

This application is a continuation of co-pending U.S. patent application Ser. No. 16/609,346, filed Oct. 29, 2019; which is a National Stage Application of International Application No. PCT/US2018/030229, filed Apr. 30, 2018; which claims the benefit of the following U.S. provisional applications: Ser. No. 62/502,714, filed May 7, 2017; and Ser. No. 62/537,057, filed Jul. 26, 2017, all of which are incorporated herein by reference in their entirety.

BACKGROUND OF THE INVENTION

The skin, or integument, is the largest organ of the human body. It is comprised of layers, including the epidermis, dermis, and hypodermis. Due, in part, to the external nature of the skin and its exposure to a panoply of environmental agents, the skin can be affected by a wide variety of conditions—some of which are more serious than others.

One skin condition, actinic keratoses (commonly known as age spots or liver spots), comprises flat, tan-, brown- or black-colored spots on the skin. The spots can vary in size and usually appear on the face, hands, shoulders and arms. While age spots are sometimes referred to as liver spots, their cause does not actually relate to liver problems. Instead, age spots are the result of excess production of the pigment melanin.

There is no definitive opinion as to why age spots develop. Currently, however, it is widely accepted that skin aging, sun exposure, or other forms of ultraviolet (UV) light exposure, such as tanning beds, can be possible causes. Furthermore, some research suggests that other factors such as viral and fungal infectious agents, immune changes in the skin, and oxidative stress caused by a variety of ROS (reactive oxygen species) molecules can play a role in the causation of keratoses.

The coloration of age spots ranges from light brown to black. Typically, their texture resembles that of the rest of the skin, and they are located on sun-exposed areas of the skin. Sometimes, the spots can have more dominant structure and can look "hilly" over the normal skin surface. In many cases, age spots are painless, pose no danger and cause no health problems. Some age spots can develop into skin cancer, however. For this reason, as well as their undesirable appearance, many people seek to have age spots removed.

Clinically, actinic keratoses present as erythematous keratotic macules, papules, and plaques. Most patients have multiple spots or lesions, and will continue to develop new lesions as a result of, for example, past UV-induced DNA damage, as well as cutaneous immunosuppression caused by continuing UV exposure.

Histologically, actinic keratoses are observed as an intraepithelial proliferation of abnormal keratinocytes. If these cells extend beyond the basement membrane, a spot can become malignant and transform into invasive squamous cell carcinoma.

The most aggressive form of actinic keratosis is keratotinic cheilitis, which appears on the lips and often transforms into squamous cell carcinoma. Squamous cell carcinoma and actinic keratosis share epidemiologic, cytologic, and molecular features. Epidemiologic data indicate that at least 10% of actinic keratosis lesions may progress to squamous cell carcinoma within 10 years, and 60% of squamous cell carcinomas arise from clinically diagnosed actinic keratoses. Individuals who are immunosuppressed as a result of cancer, chemotherapy, AIDS, or organ transplantation are also at a higher risk.

Another form of keratosis, seborrheic keratosis (SK), is a skin condition that results from a common skin growth. SK is amongst the most common cutaneous lesions, appearing in middle-aged and older adults, and affecting some 83 million Americans. This type of keratosis is mostly benign, but in very rare cases there have been reports of melanoma development within a seborrheic wart.

Seborrheic keratoses can develop almost anywhere on the skin, though most commonly on the neck, face and trunk. The growths are often round or oval shaped, and appear as flat or slightly raised spots on the skin that range in color from white to black and brown. The spots begin as small, rough bumps which thicken to look like warts, moles, actinic keratoses, or skin cancer. Seborrheic keratoses often have a waxy, "pasted-on-the-skin" look.

Seborrheic keratosis rarely causes any serious medical problems, whereas actinic keratosis often progresses to skin cancer. These two skin problems can often be differentiated based on the appearance of the lesions, although a skin biopsy may be needed to definitively diagnose the skin problems. Nonetheless, regardless of possible outcomes, both skin conditions are cosmetically undesirable for many people and furthermore can become inflamed and uncomfortable.

Prescription medications do exist for the treatment of age spots and other skin conditions related to hyperpigmentation. Some use bleaching creams to fade the age spots gradually. These prescription creams usually contain hydroquinone, with or without retinoids, such as tretinoin. Bleaching creams usually take several months to fade age spots. Other topical prescription creams, such as Imiquimod, 5-Fluorouracil, and diclofenac-based Solaraze, work by either directly attacking precancerous cells or indirectly stimulating the body's immune system to recognize precancerous cells. These creams, however, can produce a number of undesirable side-effects including redness of skin, scabbing and crusting, soreness, fever, achy joints and mouth sores.

Sometimes, procedural remedies can be utilized for age spot and/or hyperpigmentation treatment. Examples of medical procedures for treating actinic and seborrheic keratoses include laser treatment to destroy cells that produce melanin; chemical peels to burn the outer skin layer and allow new skin to grow in its place; dermabrasion, which sands off the outer layers of the skin so new skin can grow in its place; and cryosurgery, which freezes age spots with liquid nitrogen. As with prescription drugs, each of these medical procedures carries the risk of side effects and complications.

There are also many over-the-counter and cosmetic preparations and creams that are marketed for diminishing the appearance of hyperpigmented skin and age spots. These creams are not as strong as prescription creams, and the great majority may not effectively remove excessive skin pigmentation. These creams mostly contain hydroquionone, deoxyarbutin, glycolic acid, alpha hydroxy acid, or kojic acid.

To avoid the potentially more invasive and extensive treatment required if an age spot were to become malignant, preventing the conversion of large sized, multiple, or inflamed actinic keratoses into squamous cell carcinoma is important. Furthermore, from the standpoint of skin appearance, many people will go to great costs to cover up or try to diminish the appearance of both actinic and seborrheic keratoses, as well as many other hyperpigmentation conditions.

Another common skin condition is acne, or acne vulgaris, which results from the action of hormones and other impurities at the skin's oil glands and hair follicles. This condition affects about 85% of people to some degree in their lifetime. Acne is a systematic inflammatory disease resulting from blockage of sebaceous glands and hair follicles, which can become infected by the bacterium *Propionbacterium acnes* (*P. acnes*). Sebum provides a nutrient source for *P. acnes*, thus creating an ideal environment for the bacteria to proliferate and cause the occurrence of comedones, or "pimples."

Comedones are typically treated using creams or ointments containing active drug materials, such as sebum secretion inhibitors, keratinization inhibitors, antimicrobial agents and/or anti-inflammatory agents; however, many of these drug materials come with negative side effects. For example, mild inflammatory acne is usually treated with common over the counter (OTC) topical medications, including benzoyl peroxide, salicylic acid, or retinoids. Benzoyl peroxide can leave the skin with an opaque or white appearance, and can be extremely drying. Additionally, benzoyl peroxide can bleach clothing and linens that contact the treated area. Furthermore, some government regulations in various parts of the world limit or exclude its use due to its potential toxicity.

Alternatives to benzoyl peroxide are known, but are also associated with certain negative side effects. For example, women can be prescribed formulations containing estrogen and estrogen-like compounds, such as ethinyl estradiol, which are often in the form of contraceptive drugs. These drugs are typically effective as sebum secretion inhibitors, but their use can be associated with nausea, headaches, weight gain, mood swings, depression, and other side-effects.

In addition, some acne treatments use an antimicrobial component that includes chlorhexidine gluconate and benzalkonium chloride. These antimicrobials can cause irritation and extreme chapping of the skin. Furthermore, antimicrobials can lead to resistant strains developing in the wild-type fauna.

Comedolytic agents, such as salicylic acid, AHAs and the salts of both acids, are popular for exfoliating dead skin cells and opening and draining the pores. Comedolytic agents have limitations, and at high concentrations with very acidic pH, they can cause significant irritation. Comedolytic agents also have shown limited effect in preventing proliferation of *P. acnes* via antimicrobial activity and also have limited, if any, impact on directly reducing inflammation.

Skin health is crucial for a long, healthy life. Additionally, skin health is often an external expression of beauty and youthfulness. There are a wide variety of products and treatment options for treating and/or preventing a variety of skin conditions. Many of these treatments, however, utilize harsh prescriptions or procedures that have negative side-effects. Other, gentler options are simply not effective for everyone. Thus, there is a need for safe and effective cosmetic solutions that are capable of treating and/or preventing a wide range of skin conditions, including, for example, age spots and acne.

BRIEF SUMMARY OF THE INVENTION

The present invention provides microbe-based products, as well as methods of their use, in topical cosmetic compositions. More specifically, the present invention provides materials and methods for treating certain conditions of the skin using a topical cosmetic composition. Advantageously, the topical compositions and methods of the subject invention are environmentally-friendly, non-toxic, non-pharmaceutical, and cost-effective.

In certain embodiments, the skin condition is actinic keratosis, or age spots. The subject invention provides materials and methods for treating, preventing, removing and/or reducing the appearance of age spots and other hyperpigmentation conditions of the skin, by using biochemical-producing microbes and/or by-products of their growth.

In certain embodiments, the skin condition is acne. The subject invention provides materials and methods for treating, preventing, removing and/or reducing the appearance of acne and other blemish-causing conditions of the skin, by using biochemical-producing microbes and/or by-products of their growth.

In certain embodiments, the skin condition is another skin condition, such as, for example, scars, body odor, aging-related conditions (e.g., wrinkles, looseness and dryness), scalp conditions (e.g., dandruff, seborrheic dermatitis and hair loss), and in general, damage due to make-up, oil, pollution and other impurities.

In preferred embodiments, the present invention utilizes microorganisms and/or their growth by-products. For example, embodiments of the present invention provide a topical composition for treating a skin condition, wherein the composition comprises biological amphiphilic molecules (e.g., biosurfactants) and/or enzymes produced by microorganisms. In some embodiments, the microbial growth by-products can have anti-microbial properties.

In certain embodiments, the composition comprises a therapeutically effective amount of biosurfactants selected from one or more glycolipids, such as mannosylerythritol lipids (MELs), sophorolipids (SLPs), rhamnolipids (RLPs) and trehalose lipids; and/or one or more lipopeptides, such as surfactin, iturin and fengycin. In certain embodiments, the biosurfactants according to the present invention are capable of enhancing dermal penetration of other active and inactive ingredients in the composition; thus the biosurfactants can enhance the effectiveness of the treatment while serving as active ingredients themselves.

In some embodiments, the topical composition further comprises therapeutically effective amounts of resveratrol, hyaluronic acid and/or anti-comedo agents, as well as other agents known to, for example, heal, replenish, rejuvenate, moisturize, protect and/or improve the appearance and/or health of the skin in any way (e.g., to reduce the appearance of scars).

In some embodiments, the topical composition can further comprise a topically acceptable vehicle, such as a water-in-oil or oil-in-water emulsion, or an aqueous serum.

In some embodiments, the topical cosmetic composition can further comprise additional cosmetic adjuvants and additives typically found in cosmetic compositions, such as, for example, organic solvents, silicones, antimicrobials, stabilizers, thickeners, softeners, sunscreens, moisturizers or fragrances. In one embodiment, the topical composition further comprises a polymeric stabilizer, such as, for example, poly(acrylic) acid.

The topical composition can be formulated as a suspension, emulsion, hydrogel, multiphase solution, vesicular dispersion or other known forms of topical cosmetics (e.g., a lotion, cream, gel or ointment). Additionally, the topical composition can be deliverable, e.g., in a squeeze tube or a cosmetic jar, as a pen, a stick, a spray, in a wipe or via dropper.

In one embodiment, the subject invention provides methods of treating a skin condition, wherein the topical cosmetic composition is applied directly to an area of the skin where such a condition exists. In some embodiments, "applying" the composition can comprise leaving the composition on the skin, and/or rubbing it into the skin to be absorbed therein. In some embodiments, the composition can be applied to the skin for a therapeutically effective amount of time and then rinsed from the skin using, for example, water.

In certain embodiments, the topical cosmetic composition is applied, e.g., every other day, once daily, or twice daily. In some embodiments, the topical composition is applied every other day, once daily, or twice daily, for an indefinite period of time, e.g., for at least one, two, three weeks, or longer, in order to achieve and/or maintain the treatment of the skin condition.

The topical cosmetic compositions and methods of the subject invention can be used to treat and/or prevent a variety of skin conditions, including, for example, age spots, acne, scars, body odor, aging-related conditions (e.g., wrinkles, looseness and dryness), and/or scalp conditions (e.g., dandruff, seborrheic dermatitis and hair loss). Additionally, the topical cosmetic compositions can be used as a cleanser to remove makeup and other impurities from the face and skin.

In certain embodiments, the subject invention provides microbe-based compositions comprising cultivated microorganisms and/or their growth by-products. Methods of producing the microorganisms and their growth by-products are also provided.

In some embodiments, the microorganisms are biosurfactant-producing bacteria (e.g., *Bacillus subtilis, Bacillus amyloliquefaciens, Rhodococcus erythropolis, Pseudomonas aeruginosa*,) or yeasts (e.g., *Pseudozyma aphidis, Pichia* spp., or *Starmerella bombicola*). In one embodiment, the microorganisms are mutants of a desired strain or species.

In one embodiment, the subject invention provides methods of producing a biosurfactant, enzyme and/or other protein by cultivating a microbe strain of the subject invention under conditions appropriate for growth and biosurfactant, enzyme and/or protein production; and purifying the biosurfactant, enzyme and/or other protein. The cultivation process can be, for example, submerged cultivation, solid state fermentation (SSF), and/or a combination thereof.

DETAILED DESCRIPTION OF THE INVENTION

Figures 1A, 1B:
FIGS. 1A-1B show examples of the appearance of age spots on the forehead and scalp of a subject.
Figure 2:
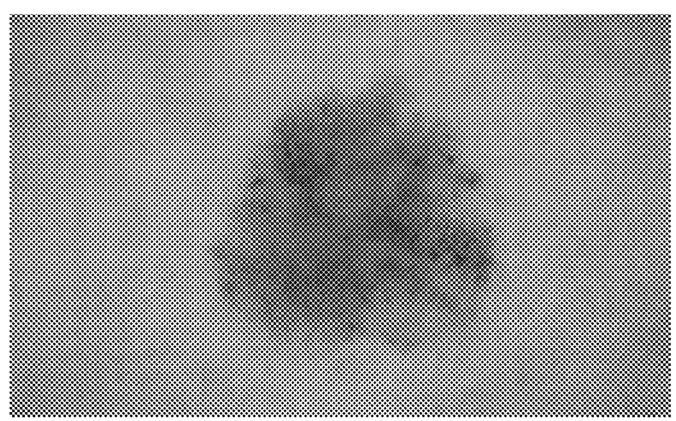
FIG. 2 shows an example of the appearance of squamous cell carcinoma on skin.
Figure 3:
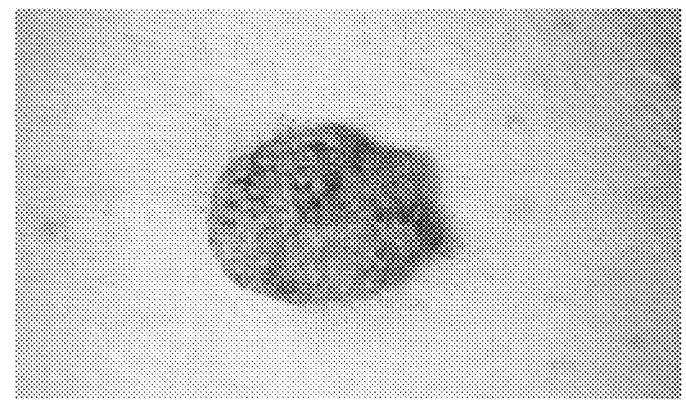
FIG. 3 shows an example of the appearance of seborrheic keratosis on skin.

The present invention provides microbe-based products, as well as methods of their use, in topical cosmetic compositions. More specifically, the present invention provides materials and methods for treating certain conditions of the skin, such as, for example, age spots and/or acne, using a topical cosmetic composition comprising microbial growth by-products.

The topical cosmetic compositions and methods of the subject invention can also be used to treat and/or prevent a variety of other skin conditions, including, for example, scars; body odor; aging-related conditions (e.g., wrinkles, looseness and dryness); and scalp issues (e.g., dandruff, seborrheic dermatitis and hair loss. Additionally, the topical cosmetic compositions can be used as a cleanser to remove makeup and other impurities (e.g., dirt and pollution) from the face and skin.

Advantageously, the topical compositions and methods of the subject invention are environmentally-friendly, non-toxic, non-pharmaceutical, and cost-effective.

Selected Definitions

As used herein, the term "skin condition" encompasses human and animal conditions, disorders, or diseases affecting skin. Such skin conditions include, but are not limited to, conditions involving the epidermis, dermis (including connective tissue, sebaceous glands and hair follicles), and the subcutaneous tissue (hypodermis). Symptoms of skin conditions can include, for example, acneiform symptoms, pigmentation or loss thereof, flushing, inflammation, wrinkles, dryness, looseness, thickening, scaling, scarring, flaking, rash, hives, blisters, ulcers, peeling, hair loss and other changes in the appearance of the skin. Skin conditions that can, in certain embodiments, be treated and/or preventing using compositions, products and methods described herein include, but are not limited to, acne, blemishes, rosacea, folliculitis, carcinoma, melanoma, perioral dermatitis, cellulitis, carbuncles, photodamage, skin aging (e.g., wrinkles and dryness), age spots, scars, lupus, psoriasis, ichtiosis, atopic dermatitis, chronic wounds, bed sores, keratosis piralis, sebaceous cysts, vitiligo, melisma, warts, inflammatory dermatoses, post inflammatory hyperpigmentation, keratoses, eczema, xerosis, pruritis, lichen planus, nodular prurigo, microbial infection, body odor, scalp conditions and miliaria.

As used herein, the term "subject" refers to an animal, especially a mammal, receiving medical treatment, including over-the-counter medical treatment and preventative care. The preferred subject in the context of this invention is a human patient. The subject can be of any age or stage of development including baby, infant, toddler, preteen, teenager, and adult. The subject can be any gender.

As used herein, "cosmetically acceptable," "topically acceptable" and "dermatologically acceptable" are used interchangeably and are intended to mean that a particular component is safe and non-toxic for application to a human integument (e.g., skin) at the levels employed. In one embodiment, the components of the composition are recognized as being Generally Regarded as Safe (GRAS).

As used herein, the terms "therapeutically effective amount," "effective amount," and "effective dose" are used to refer to an amount of something (e.g., a compound, a composition, time) is capable of treating a condition or disorder in a subject. The actual amount will vary depending on a number of factors including, but not limited to, the particular condition or disorder being treated, the severity of the condition, the size, age, and health of the subject, and the route of administration.

As used herein, the term "treatment" refers to eradicating, reducing, ameliorating, or reversing, a degree, sign or symptom of a condition or disorder to any extent, and includes, but does not require, a complete cure of the condition or disorder. Treating can be curing, improving, or partially ameliorating a disorder.

As used herein, "preventing" a condition or disorder refers to avoiding, delaying, forestalling, or minimizing the onset of a particular sign or symptom of the condition or disorder. Prevention can, but is not required to be, absolute or complete, meaning the sign or symptom may still develop at a later time. Prevention can include reducing the severity of the onset of such a condition or disorder, and/or inhibiting the progression of the condition or disorder to a more severe condition or disorder. For example, in one embodiment, preventing hyperpigmentation can refer to avoiding, delaying, forestalling, or minimizing one or more unwanted features associated with skin hyperpigmentation, such as reducing the darkness or size of hyperpigmented areas that eventually develop. As another example, in one embodiment, preventing acne can refer to avoiding, delaying, forestalling, or minimizing one or more unwanted features associated with acne, such as reducing the number, darkness, and/or size of comedones that eventually develop, lessening the severity of acne that eventually develops, and/or completely or almost completely preventing the growth of *P. acnes*, the development of acne blemishes, and the other symptoms of acne.

As used herein, a "microbe-based composition" means a composition that comprises components that were produced as the result of the growth of microorganisms or other cell cultures. Thus, the microbe-based composition may comprise the microbes themselves and/or by-products of microbial growth (e.g., biosurfactants, solvents and/or enzymes). The cells may be in a vegetative state or in spore form, or a mixture of both. The cells may be planktonic or in a biofilm form, or a mixture of both. The cells may be intact or lysed. The cells can be present, with broth in which they were grown, at, for example, a concentration of $1\times10^4$, $1\times10^5$, $1\times10^6$, $1\times10^7$, $1\times10^8$, $1\times10^9$, $1\times10^{10}$, or $1\times10^{11}$ or more cells per milliliter of the composition. In one embodiment, the microbe-based composition may comprise only the broth in which the cells were grown, with the cells removed. The by-products of growth may be present in the broth and can include, for example, metabolites, cell membrane components, expressed proteins, and/or other cellular components.

The subject invention further provides "microbe-based products," which are products that are to be applied in practice to achieve a desired result. The microbe-based product can be simply the microbe-based composition harvested from the microbe cultivation process. Alternatively, the microbe-based product may comprise further ingredients that have been added. These additional ingredients can include, for example, stabilizers, buffers, appropriate carriers, such as water, salt solutions, or any other appropriate carrier, added nutrients to support further microbial growth, non-nutrient growth enhancers, and/or agents that facilitate tracking of the microbes and/or the composition in the environment to which it is applied. The microbe-based product may also comprise mixtures of microbe-based compositions. The microbe-based product may also comprise one or more components of a microbe-based composition that have been processed in some way such as, but not limited to, filtering, centrifugation, lysing, drying, purification and the like.

A "metabolite" refers to any substance produced by metabolism or a substance necessary for taking part in a particular metabolic process. A metabolite can be an organic compound that is a starting material (e.g., glucose), an intermediate (e.g., acetyl-CoA) in, or an end product (e.g., n-butanol) of metabolism. Examples of metabolites can include, but are not limited to, enzymes, toxins, acids, solvents, alcohols, proteins, carbohydrates, vitamins, minerals, microelements, amino acids, polymers, and surfactants.

As used herein, the terms "isolated" or "purified," when used in connection with biological or natural materials such as nucleic acid molecules, polynucleotides, polypeptides, proteins, organic compounds, such as small molecules, microorganism cells/strains, or host cells, means the material is substantially free of other compounds, such as cellular material, with which it is associated in nature. That is, the materials do not occur naturally without these other compounds and/or have different or distinctive characteristics compared with those found in the native material.

In certain embodiments, purified compounds are at least 60% by weight the compound of interest. Preferably, the preparation is at least 75%, more preferably at least 90%, and most preferably at least 99% or 100% (w/w) of the desired compound by weight. Purity is measured by any appropriate standard method, for example, by column chromatography, thin layer chromatography, or high-performance liquid chromatography (HPLC) analysis.

As used herein, "surfactant" means a compound that lowers the surface tension (or interfacial tension) between two liquids or between a liquid and a solid. Surfactants act as detergents, wetting agents, emulsifiers, foaming agents, and/or dispersants. By "biosurfactant" is meant a surface-active substance produced by a living cell.

The transitional term "comprising," which is synonymous with "including," or "containing," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

Unless specifically stated or obvious from context, as used herein, the term "or" is understood to be inclusive. Unless specifically stated or obvious from context, as used herein, the terms "a," "an" and "the" are understood to be singular or plural.

Unless specifically stated or obvious from context, as used herein, the term "about" is understood as within a range of normal tolerance in the art, for example, within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

Other features and advantages of the invention will be apparent from the following description of the preferred embodiments thereof, and from the claims. All references cited herein are hereby incorporated by reference.

Topical Cosmetic Compositions

The subject invention provides skin care compositions and methods of their use. In particular, the subject invention provides skin care and cosmetic products that can treat and/or prevent a skin condition, including age spots, acne, scars, body odor, aging-related conditions, scalp conditions, and/or others described herein. In certain embodiments, the present invention utilizes microbial growth by-products.

Particularly, embodiments of the present invention provide a topical composition for treating human skin conditions, wherein the composition comprises biological amphiphilic molecules (e.g., biosurfactants) produced by the cultivation of biochemical-producing microorganisms. In some embodiments, the biological amphiphilic molecules are utilized in a crude form, wherein the molecule is present in the broth in which the microorganism is cultivated and is collected therefrom without purification. The crude form can comprise, for example, at least 20%, 30%, 40%, 50%, 60%, 70% or 80% amphiphilic molecule in broth. In some embodiments, the biological amphiphilic molecules have been purified from the products of cultivation.

In certain embodiments, the composition can comprise a therapeutically effective amount of glycolipids, such as mannosylerythritol lipids (MELs), sophorolipids (SLPs), trehalose lipids (TLs) and rhamnolipids (RLP); and/or lipopeptides, such as surfactin, iturin A, and fengycin. In one embodiment, the composition can comprise a combination of any of these biosurfactants.

The biological amphiphilic molecules according to the present invention are capable of one or more of the following: killing pathogenic agents in the skin, modulating the skin's immune system, killing melanocytes to allow for replacement cells to grow, reducing oxidative stress, enhancing multiplication and function of keratinocytes and fibroblasts, and enhancing dermal penetration of both the, e.g., biosurfactants, and one or more other active ingredients in the composition. Thus, while providing therapeutic benefits themselves, these beneficial molecules can also enhance the overall effectiveness of the topical composition in treating skin conditions related to, for example, hyperpigmentation or the presence of microbial agents.

MELs and SLPs are part of a glycolipid class of biosurfactants produced by a variety yeasts. MELs are produced mainly by the yeast genus *Pseudozyma*, with significant variability among MEL structures produced by each species. MELs are non-toxic and are stable at wide temperatures and pH ranges. Furthermore, MELs can be used without any additional preservatives.

In preferred embodiments, MEL concentration in the topical cosmetic composition ranges from 0.001% to 90% of the total composition by weight, from 0.01% to 50%, from 0.05% to 10%, and preferably from 0.1% to 2.0%.

SLPs are produced in large quantity by several nonpathogenic yeast species, the most studied of which is Starmerella bombicola. SLPs have environmental compatibility, high biodegradability, low toxicity, high selectivity and specific activity in a broad range of temperature, pH and salinity conditions.

In preferred embodiments, SLP concentration in the topical cosmetic composition ranges from 0.001% to 90% of the total composition by weight, from 0.01% to 50%, from 0.05% to 10%, and preferably from 0.1% to 2.0%. In one embodiment, the topical composition comprises SLP in acidic form.

RLPs are glycolipids produced mainly by Pseudomonas bacteria. They are natural emulsifiers, and can be used according to the subject invention to replace non-biological surfactants, such as sodium lauryl sulfate, sodium dodecyl sulfate and sodium laureth sulfate, in a cosmetic composition. Furthermore, RLPs can be formulated to increase moisture retention or to lubricate skin, minimize the appearance of wrinkles, and increase smoothness of skin. Even further, RLPs can be used as antibacterial (Gram-positive) and antifungal agents.

In preferred embodiments, RLP concentration in the topical cosmetic composition ranges from 0.001% to 90% of the total composition by weight, from 0.01% to 50%, from 0.05% to 10%, and preferably from 0.1% to 2.0%.

Trehalose lipids (TLs) are glycolipids produced by, for example, the bacteria *Rhodococcus erythropolis*. TLs possess emulsifying and dispersing characteristics. They exhibit increased levels of surface activity and have certain antiviral and antimicrobial properties.

In preferred embodiments, TL concentration in the topical cosmetic composition ranges from 0.001% to 90% of the total composition by weight, from 0.01% to 50%, from 0.05% to 10%, and preferably from 0.1% to 2.0%.

Surfactin is a lipopeptide produced by certain bacterial strains, mainly Bacillus subtilis. Surfactin has high level surface activating function, and is extremely hydrophilic, forming a transparent gel at a wider range of concentrations than other biosurfactants. This biosurfactant can act as a skin penetration agent for cosmetic products, a foaming agent and an emulsifier.

Furthermore, surfactin exhibits effective antibacterial (Gram-negative), antifungal and antiviral properties.

In preferred embodiments, surfactin concentration in the topical cosmetic composition ranges from 0.001% to 90% of the total composition by weight, from 0.01% to 50%, from 0.05% to 10%, from 0.1% to 5.0%, and preferably from 0.01% to 2.0%.

Additional biological amphiphilic molecules useful according to the present invention include mannoprotein, beta-glucan and other metabolites that have bio-emulsifying and surface/interfacial tension-reducing properties.

In some embodiments, the topical cosmetic composition can comprise therapeutically effective amounts of enzymes and/or proteins produced by microorganisms. For example, from about 0.001% to about 20% by weight, preferably from about 0.01% to about 15% by weight, or from about 0.05% to about 10% by weight, of one or more enzymes and/or proteins can be included. These can include, but are not limited to, exo-beta-1,3-glucanase, "killer toxins," chitinase, esterases, lipases, glycosidases, amylases, and proteases beneficial for improving skin health.

In some embodiments, the topical composition further comprises therapeutically effective amounts of resveratrol. In certain embodiments, amount of resveratrol with respect to total weight of the subject topical composition ranges from 0.001 to 5.0% by weight, more preferably from 0.05 to 2.0% by weight, and most preferably from 0.2 to 1.0% by weight.

Resveratrol is a naturally-occurring substance found in the skin of fruits such as grapes, blueberries, raspberries and mulberries. It is reported to be an extremely potent antioxidant, a modulator of genetic expression via signal transduction, an inhibitor of inflammatory mediators and, by acting on diverse mechanisms simultaneously, it has been emphasized as a promising, multi-target, anticancer agent, relevant in both cancer prevention and treatment. Additionally, resveratrol has unique skin bleaching abilities, as it reduces the synthesis of melanin.

In one embodiment, the topical composition can further comprise a polymeric stabilizer, such as, for example, from about 0.01% to about 5.0%, or from about 0.05% to about 2.0%, or from about 0.5% to about 1.0% poly(acrylic) acid. Poly(acrylic) acid helps to prevent resveratrol from crystallizing.

In some embodiments, the topical composition further comprises therapeutically effective amounts of hyaluronic acid. Hyaluronic acid is produced naturally in the fibroblasts of human skin, and can be used in the healing of skin wounds such as burns and ulcers, and as a skin moisturizer. Hyaluronic acid can aide in moisture retention, tissue repair, and holding together the collagen and elastin that make up the structural components of skin. It can also help create a protective barrier against undesirable microorganisms.

In one embodiment, the topical composition comprises from about 0.01% to about 10.0%, or from about 0.05% to about 8.0%, from about 0.5% to about 5.0%, or from about 1.0% to about 3.0% by weight hyaluronic acid.

In some embodiments, the topical composition can further comprise a topically or cosmetically acceptable vehicle.

The cosmetically acceptable vehicle may be in the form of an emulsion. Non-limiting examples of suitable emulsions include water-in-oil emulsions, oil-in-water emulsions, silicone-in-water emulsions, water-in-silicone emulsions, wax-in-water emulsions, water-oil-water triple emulsions or the like having the appearance of a cream, gel or microemulsions.

As used herein, the term "oil" includes silicone oils unless otherwise indicated. The emulsion may include an emulsifier, such as a nonionic, anionic or amphoteric surfactant, or a gallant, typically in an amount from about 0.001% to about 5% by weight.

The cosmetically acceptable vehicle may include water; vegetable oils; mineral oils; ester oils such as octal palmitate, isopropyl myristate and isopropyl palmitate; ethers such as dicapryl ether and dimethyl isosorbide; alcohols such as ethanol and isopropanol; fatty alcohols such as cetyl alcohol, cetearyl alcohol, stearyl alcohol and behenyl alcohol; isoparaffins such as isooctane, isododecane (IDD) and isohexadecane; silicone oils such as cyclomethicone, dimethicone, dimethicone cross-polymer, polysiloxanes and their derivatives, preferably organomodified derivatives including PDMS, dimethicone copolyol, dimethiconols, and amodimethiconols; hydrocarbon oils such as mineral oil, petrolatum, isoeicosane and polyolefins, e.g., (hydrogenated) polyisobutene; polyols such as propylene glycol, glycerin, butylene glycol, pentylene glycol, hexylene glycol, caprylyl glycol; waxes such as beeswax, carnauba, ozokerite, microcrystalline wax, polyethylene wax, and botanical waxes; or any combinations or mixtures of the foregoing. Aqueous vehicles may include one or more solvents miscible with water, including lower alcohols, such as ethanol, isopropanol, and the like. The vehicle may comprise from about 1% to about 99% by weight of the composition, from 10% to about 85%, from 25% to 75%, or from 50% to about 65%.

In some embodiments, the topical cosmetic composition can further comprise additional cosmetic adjuvants and additives commonly included in cosmetic compositions, such as, for example, organic solvents, stabilizers, silicones, thickeners, softeners, sunscreens, moisturizers or fragrances. The amounts of each ingredient, whether active or inactive, are those conventionally used in the cosmetic field to achieve their intended purpose, and typically range from about 0.0001% to about 25%, or from about 0.001% to about 20% of the composition, although the amounts may fall outside of these ranges. The nature of these ingredients and their amounts must be compatible with the production and function of the compositions of the disclosure.

In one embodiment, the composition may include additional skin actives, including but not limited to, retinoids, botanicals, keratolytic agents, desquamating agents, keratinocyte proliferation enhancers, collagenase inhibitors, elastase inhibitors, depigmenting agents, anti-inflammatory agents, steroids, anti-acne agents, antioxidants, and advanced glycation end-product (AGE) inhibitors, to name but a few.

In one embodiment, the composition may include additional anti-aging components, including, but not limited to, botanicals (e.g., *Butea frondosa* extract, Aloe vera extract); phytol; phytonic acid; phospholipids; silicones; petrolatum; triglycerides; omerga fatty acids; retinoids; hydroxy acids (including alpha-hydroxy acids and beta-hydroxy acids), salicylic acid and alkyl salicylates; exfoliating agents (e.g., glycolic acid, 3,6,9-trioxaundecanedioic acid, etc.), estrogen synthetase stimulating compounds (e.g., caffeine and derivatives); compounds capable of inhibiting 5 alpha-reductase activity (e.g., linolenic acid, linoleic acid, finasteride, and mixtures thereof); and barrier function enhancing agents (e.g., ceramides, glycerides, cholesterol and its esters, alpha-hydroxy and omega-hydroxy fatty acids and esters thereof.)

Exemplary retinoids include, without limitation, retinoic acid (e.g., all-trans, or 9-cis, or 13-cis), and derivatives thereof, retinaldehyde, retinol (Vitamin A) and esters thereof, such as retinyl palmitate, retinyl acetate and retinyl propionate, and salts thereof. When present, the retinoids will typically be included in amounts from about 0.0001% to about 5% by weight, more typically from about 0.01% to about 2.5% by weight, or from about 0.1% to about 1.0% by weight. Compositions according to this embodiment will typically include an antioxidant such as ascorbic acid and/or BHT and/or a chelating agent such as EDTA or a salt thereof (e.g., disodium EDTA).

In another embodiment, the topical compositions of the present invention may also include one or more of the following: a skin penetration enhancer; an emollient, such as isopropyl myristate, petrolatum, volatile or non-volatile silicones oils (e.g., methicone, dimethicone), ester oils, mineral oils, and fatty acid esters; a humectant, such as glycerin, hexylene glycol or caprylyl glycol; a skin plumper, such as palmitoyl oligopeptide, collagen, collagen and/or glycosaminoglycan (GAG) enhancing agents; a sunscreen, such as avobenzone or octyl methoxycinnamate; an exfoliating agent; and an antioxidant.

Suitable exfoliating agents include, for example, alpha-hydroxy acids, beta-hydroxy acids, oxa-acids, oxadiacids, and their derivatives such as esters, anhydrides and salts thereof. Suitable hydroxy acids include, for example, glycolic acid, lactic acid, malic acid, tartaric acid, citric acid, 2-hydroxyalkanoic acid, mandelic acid, salicylic acid and derivatives thereof. One exemplary exfoliating agent is glycolic acid. When present, the exfoliating agent may comprise from about 0.001% to about 20% by weight of the composition.

Examples of antioxidants that may be used in the present compositions include compounds having phenolic hydroxy functions, such as ascorbic acid and its derivatives/esters; beta-carotene; catechins; curcumin; ferulic acid derivatives (e.g., ethyl ferulate, sodium ferulate); gallic acid derivatives (e.g., propyl gallate); lycopene; reductic acid; rosmarinic acid; tannic acid; tetrahydrocurcumin; tocopherol and its derivatives, including tocopheryl acetate; uric acid; or any mixtures thereof. Other suitable antioxidants are those that have one or more thiol functions (—SH), in either reduced or non-reduced form, such as glutathione, lipoic acid, thioglycolic acid, and other sulfhydryl compounds. The antioxidant may be inorganic, such as bisulfites, metabisulfites, sulfites, or other inorganic salts and acids containing sulfur. Antioxidants may comprise, individually or collectively, from about 0.001% to about 10% (w/w), or from about 0.01% to about 5% (w/w) of the total weight of the composition.

Non-biological surfactants can also be added to the formulation. Examples of surfactants include, but are not limited to, alkyl sulfates, alkyl ether sulfates (e.g., sodium/ammonium lauryl sulfates and sodium/ammonium laureth sulfates), amphoterics (e.g., amphoacetates and amphopropionates), sulfosuccinates, alkyl polyglucosides, betaines (e.g., cocamidopropul betaine (CAPB)), sultaines, sacrosinates, isethionates, taurates, ethoxylated sorbitan esters, alkanolamides and amino-acid based surfactants.

Viscosity modifiers can also be added to the compositions, including, for example, cocamide DEA, oleamide DEA, sodium chloride, cellulosic polymers, polyacrylates, ethoxylated esters, alcohol, glycols, xylene sulfonates, polysorbate 20, alkanolamides, and cellulose derivatives (e.g., hydroxypropyl methylcellulose and hydroxyethyl cellulose).

Polymers can also be added, include, for example, xanthan gum guar gum, polyquaternium-10, PEG-120 methyl glucose dioleate, PEG-150 distearate, PEG-150 polyglyceryl-2 tristearate and PEG-150 pentaerythrityl tetrastearate Other additives include: vitamins, such as tocopherol and ascorbic acid; vitamin derivatives such as ascorbyl monopalmitate, tocopheryl acetate, and Vitamin E palmitate; thickeners such as hydroxyalkyl cellulose, carboxymethylcellulose, carbombers, and vegetable gums such as xanthan gum; gelling agents, such as ester-terminated polyester amides; structuring agents; metal chelating agents such as EDTA or salts thereof; pigments; colorants; proteins, such as lactoferrin; and pH adjusters (citric acid, ethanolamine, sodium hydroxide, etc.).

The composition may optionally comprise other components known to those skilled in the art including, but not limited to, film formers, moisturizers, minerals, viscosity and/or rheology modifiers, anti-acne agents, insect repellents, skin cooling compounds, skin protectants, lubricants, fragrances, preservatives, stabilizers, and mixtures thereof. In addition to the foregoing, the cosmetic compositions of the invention may contain any other compound for the treatment of skin conditions or disorders.

In addition, the compositions contemplated by this disclosure can include one or more compatible cosmetically acceptable adjuvants commonly used and known by the skilled practitioner, such as colorants, pearls, chromalites, micas, pigments, dyes, fragrances, emollients, humectants, preservatives, conditioners, vitamins, chelators, thickeners, anesthetics, anti-allergenics, antifungals, antimicrobials, other anti-inflammatory agents, antioxidants, antiseptics, depigmenting agents, film formers, insect repellents, pharmaceutical agents, photostabilizing agents, sunscreens, stabilizers, surfactants, thickeners, viscosity modifiers, and botanicals. The topical compositions of the present disclosure may also include a skin penetration enhancer, a surface smoother, a skin plumper, an optical diffuser, an exfoliation promoter, and an antioxidant. Details with respect to these and other suitable cosmetic ingredients can be found in the "International Cosmetic Ingredient Dictionary and Handbook," 10th Edition (2004), published by the Cosmetic, Toiletry, and Fragrance Association (CTFA), at pp. 2177-2299, which is herein incorporated by reference in its entirety. The amounts of these various substances are those that are conventionally used in the cosmetic or pharmaceutical fields, for example, they can constitute from about 0.01% to about 20% of the total weight of the composition.

A sunscreen or combination of sunscreens may be included to protect the skin from both UVA and UVB rays. Among the sunscreens that can be employed in the present compositions are avobenzone, cinnamic acid derivatives (such as octylmethoxy cinnamate), octyl salicylate, oxybenzone, octocrylene, titanium dioxide, zinc oxide, or any mixtures thereof. The sunscreen may be present from about 1 wt % to about 30 wt % of the total weight of the composition.

Additionally, the composition may contain compounds capable of bleaching keratoses dark and reddish colors and the compounds that can improve the skin turgor and increase the penetration of other compounds into the deeper layers of the skin.

The composition may be formulated as a suspension, emulsion, hydrogel, multiphase solution, vesicular dispersion or in any other known form of cosmetic topical skin composition.

In certain embodiments, the topical cosmetic composition may be formulated so that it can be applied, for example, via pen, tube, bottle, brush, stick, sponge, cotton swab, towelette (wipe), sprayer, dropper, hand or finger.

The composition may be formulated in a variety of product forms, such as, for example, a lotion, cream, serum, spray, aerosol, liquid cake, ointment, essence, gel, paste, patch, pencil, powder, towelette, soap, shampoo, conditioner, stick, foam, mousse, elixir or concentrate. In preferred embodiments, the composition is formulated so that is particularly suitable for topical administration to the skin.

The composition can be formulated within a wide range of pH levels. In one embodiment, the pH of the topical composition ranges from 1.0 to 13.0. In some embodiments, the pH of the topical composition ranges from 2.0 to 12.0. Other pH ranges suitable for the subject composition include from 3.5 to 7.0, or from 7.0 to 10.5. Suitable pH adjusters such as sodium hydroxide, citric acid and triethanolamine may be added to bring the pH within the desired range.

Growth of Microbes and Production of Microbial Growth By-Products

The subject invention provides methods for cultivating microorganisms and production of microbial metabolites and/or other by-products of microbial growth. The microbial cultivation systems would typically use submerged culture fermentation; however, surface culture and hybrid systems can also be used. As used herein "fermentation" refers to growth of cells under controlled conditions. The growth could be aerobic or anaerobic.

In one embodiment, the subject invention provides materials and methods for the production of biomass (e.g., viable cellular material), extracellular metabolites (e.g. small molecules and excreted proteins), residual nutrients and/or intracellular components (e.g. enzymes and other proteins).

The microbe growth vessel used according to the subject invention can be any fermenter or cultivation reactor for industrial use. In one embodiment, the vessel may have functional controls/sensors or may be connected to functional controls/sensors to measure important factors in the cultivation process, such as pH, oxygen, pressure, temperature, agitator shaft power, humidity, viscosity and/or microbial density and/or metabolite concentration.

In a further embodiment, the vessel may also be able to monitor the growth of microorganisms inside the vessel (e.g., measurement of cell number and growth phases). Alternatively, a daily sample may be taken from the vessel and subjected to enumeration by techniques known in the art, such as dilution plating technique. Dilution plating is a simple technique used to estimate the number of microbes in a sample. The technique can also provide an index by which different environments or treatments can be compared.

In one embodiment, the method includes supplementing the cultivation with a nitrogen source. The nitrogen source can be, for example, potassium nitrate, ammonium nitrate ammonium sulfate, ammonium phosphate, ammonia, urea, and/or ammonium chloride. These nitrogen sources may be used independently or in a combination of two or more.

The method can provide oxygenation to the growing culture. One embodiment utilizes slow motion of air to remove low-oxygen containing air and introduce oxygenated air. The oxygenated air may be ambient air supplemented daily through mechanisms including impellers for mechanical agitation of the liquid, and air spargers for supplying bubbles of gas to the liquid for dissolution of oxygen into the liquid.

The method can further comprise supplementing the cultivation with a carbon source. The carbon source is typically a carbohydrate, such as glucose, sucrose, lactose, fructose, trehalose, mannose, mannitol, and/or maltose; organic acids such as acetic acid, fumaric acid, citric acid, propionic acid, malic acid, malonic acid, and/or pyruvic acid; alcohols such as ethanol, propanol, butanol, pentanol, hexanol, isobutanol, and/or glycerol; fats and oils such as soybean oil, rice bran oil, olive oil, corn oil, sesame oil, and/or linseed oil; etc. These carbon sources may be used independently or in a combination of two or more.

In one embodiment, growth factors and trace nutrients for microorganisms are included in the medium. This is particularly preferred when growing microbes that are incapable of producing all of the vitamins they require. Inorganic nutrients, including trace elements such as iron, zinc, copper, manganese, molybdenum and/or cobalt may also be included in the medium. Furthermore, sources of vitamins, essential amino acids, and microelements can be included, for example, in the form of flours or meals, such as corn flour, or in the form of extracts, such as yeast extract, potato extract, beef extract, soybean extract, banana peel extract, and the like, or in purified forms. Amino acids such as, for example, those useful for biosynthesis of proteins, can also be included, e.g., L-Alanine.

In one embodiment, inorganic salts may also be included. Usable inorganic salts can be potassium dihydrogen phosphate, dipotassium hydrogen phosphate, disodium hydrogen phosphate, magnesium sulfate, magnesium chloride, iron sulfate, iron chloride, manganese sulfate, manganese chloride, zinc sulfate, lead chloride, copper sulfate, calcium chloride, calcium carbonate, and/or sodium carbonate. These inorganic salts may be used independently or in a combination of two or more.

In some embodiments, the method for cultivation may further comprise adding additional acids and/or antimicrobials in the liquid medium before and/or during the cultivation process. Antimicrobial agents or antibiotics are used for protecting the culture against contamination.

Additionally, antifoaming agents may also be added to prevent the formation and/or accumulation of foam when gas is produced during cultivation.

The pH of the mixture should be suitable for the microorganism of interest. Buffers, and pH regulators, such as carbonates and phosphates, may be used to stabilize pH near a preferred value. When metal ions are present in high concentrations, use of a chelating agent in the liquid medium may be necessary.

The method and equipment for cultivation of microorganisms and production of the microbial by-products can be performed in a batch, quasi-continuous, or continuous processes.

In one embodiment, the method for cultivation of microorganisms is carried out at about 5° to about 100° C., preferably, 15 to 60° C., more preferably, 25 to 50° C. In a further embodiment, the cultivation may be carried out continuously at a constant temperature. In another embodiment, the cultivation may be subject to changing temperatures.

In one embodiment, the equipment used in the method and cultivation process is sterile. The cultivation equipment such as the reactor/vessel may be separated from, but connected to, a sterilizing unit, e.g., an autoclave. The cultivation equipment may also have a sterilizing unit that sterilizes in situ before starting the inoculation. Air can be sterilized by methods know in the art. For example, the ambient air can pass through at least one filter before being introduced into the vessel. In other embodiments, the medium may be pasteurized or, optionally, no heat at all added, where the use of low water activity and low pH may be exploited to control bacterial growth.

In one embodiment, the subject invention provides methods of producing a biosurfactant, enzyme and/or other protein by cultivating a microbe strain of the subject invention under conditions appropriate for growth and biosurfactant, enzyme and/or protein production; and purifying the biosurfactant, enzyme and/or other protein.

In one embodiment, the subject invention further provides a method for producing other microbial metabolites such as ethanol, lactic acid, beta-glucan, proteins, peptides, metabolic intermediates, polyunsaturated fatty acid, and lipids. The metabolite content produced by the method can be, for example, at least 20%, 30%, 40%, 50%, 60%, 70%, 80%, or 90%.

The biomass content of the fermentation broth may be, for example from 5 g/l to 180 g/l or more. In one embodiment, the solids content of the broth is from 10 g/l to 150 g/l.

The microbial growth by-product produced by microorganisms of interest may be retained in the microorganisms or secreted into the liquid medium. In another embodiment, the method for producing microbial growth by-product may further comprise steps of concentrating and purifying the microbial growth by-product of interest. In a further embodiment, the liquid medium may contain compounds that stabilize the activity of microbial growth by-product.

In one embodiment, all of the microbial cultivation composition is removed upon the completion of the cultivation (e.g., upon, for example, achieving a desired cell density, or density of a specified metabolite in the broth). In this batch procedure, an entirely new batch is initiated upon harvesting of the first batch.

In another embodiment, only a portion of the fermentation product is removed at any one time. In this embodiment, biomass with viable cells remains in the vessel as an inoculant for a new cultivation batch. The composition that is removed can be a cell-free broth or contain cells. In this manner, a quasi-continuous system is created.

Advantageously, the method does not require complicated equipment or high energy consumption. The microorganisms of interest can be cultivated at small or large scale on site and utilized, even being still-mixed with their media. Similarly, the microbial metabolites can also be produced at large quantities at the site of need.

The microorganisms grown according to the systems and methods of the subject invention can be, for example, bacteria, yeast and/or fungi. These microorganisms may be natural, or genetically modified microorganisms. For example, the microorganisms may be transformed with specific genes to exhibit specific characteristics. The microorganisms may also be mutants of a desired strain. As used herein, "mutant" means a strain, genetic variant or subtype of a reference microorganism, wherein the mutant has one or more genetic variations (e.g., a point mutation, missense mutation, nonsense mutation, deletion, duplication, frame-shift mutation or repeat expansion) as compared to the reference microorganism. Procedures for making mutants are well known in the microbiological art. For example, UV mutagenesis and nitrosoguanidine are used extensively toward this end.

In preferred embodiments, the microbes are biosurfactant-producing and/or enzyme-producing microorganisms. In one embodiment, the microorganism is a yeast or fungus. Yeast and fungus species suitable for use according to the current invention, include, for example, *Candida, Saccharomyces* (*S. cerevisiae, S. boulardii sequela, S. torula*), *Issatchenkia, Kluyveromyces, Pichia, Wickerhamomyces* (e.g., *W. anomalus*), *Starmerella* (e.g., *S. bombicola*), *Mycorrhiza, Mortierella, Phycomyces, Blakeslea, Thraustochytrium, Phythium, Entomophthora, Aureobasidium pullulans, Pseudozyma aphidis, Aspergillus* and/or *Rhizopus* spp.

In one embodiment, the microorganism is a killer yeast. As used herein, "killer yeast" means a strain of yeast characterized by its secretion of toxic proteins or glycoproteins, to which the strain itself is immune. The exotoxins secreted by killer yeasts are capable of killing other strains of yeast, fungi, or bacteria. For example, microorganisms that can be controlled by killer yeast include Fusarium and other filamentous fungi. Such yeasts can include, but are not limited to, *Wickerhamomyces* (e.g., *W. anomalus*), *Pichia* (e.g., *P. anomala, P. guielliermondii, P. occidentalis, P. kudriavzevii*), *Hansenula, Saccharomyces, Hanseniaspora*, (e.g., *H. uvarum*), *Ustilago maydis, Debaryomyces hansenii, Candida, Cryptococcus, Kluyveromyces, Torulopsis, Ustilago, Williopsis, Zygosaccharomyces* (e.g., *Z. bailii*), and others.

In one embodiment, the microbe used for the present invention is *Pseudozyma aphidis. Pseudozyma aphidis* is an efficient producer of mannosylerythritol lipids (MELs).

In one embodiment, the microbe can be chosen from strains of killer yeast. In even more preferred embodiments, the microbes are *Pichia* strains, including, for example, *P. anomalus* (*Wickerhamomyces anomalus*), *P. kudriavzevii* (*Wickerhamomyces kudriavzevii*), and/or *P. guilliermondii* (*Meyerozyma guilliermondii*).

In one embodiment, the microbial strain is *Starmerella bombicola*, which is an efficient producer of sophorolipids (SLPs).

In one embodiment, the microorganisms are bacteria, including Gram-positive and Gram-negative bacteria. The bacteria may be, for example *Agrobacterium radiobacter, Arthrobacter, Azobacter* (e.g., *A. vinelandii, A. chroococcum*), *Azospirillum brasiliensis, Bacillus* (e.g., *B. subtilis, B. licheniformis, B. firmus, B. laterosporus, B. megaterium, B. amyloliquifaciens*), *Clostridium* (e.g., *C. butyricum, C. tyrobutyricum, C. acetobutyricum, Clostridium* NIPER 7, and *C. beijerinckii*), *ordonia, Mycobacterium, Nocardia, Pseudomonas* (e.g., *P. chlororaphis* subsp. *aureofaciens* (*Kluyver*), *P. aeruginosa*), *Ralslonia eulropha, Rhodococcus* (e.g., *Rhodococcus erythropolis*), *Rhodospirillum rubrum, Rhizobium* and/or, *Sphingomonas paucimobilis,*

In one embodiment, the microbe is a non-pathogenic strain of *Pseudomonas* (e.g., *P. aeruginosa*). Preferably, the strain is a producer of rhamnolipid biosurfactants (RLP).

In one embodiment, the microbe is *Rhodococcus erythropolis*, which is an effective producer of trehalose lipids (TLs).

In one embodiment, the microorganism is a strain of *B. subtilis*, such as, for example, *B. subtilis* var. *lotuses* B1 or B2, which are effective producers of, for example, surfactin and iturin. This specification incorporates by reference International Publication No. WO 2017/044953 A1 to the extent it is consistent with the teachings disclosed herein.

In another embodiment, the microorganism is a strain of Bacillus amyloliquefaciens, which is also an effective producer of surfactin.

Other microbial strains including, for example, other strains capable of accumulating significant amounts of, for example, glycolipid-biosurfactants or lipopeptide-biosurfactants can be used in accordance with the subject invention. Additional metabolites useful according to the present invention include mannoprotein, beta-glucan and other biological amphiphilic molecules that have bio-emulsifying and surface/interfacial tension-reducing properties.

Preparation of Microbe-Based Products

One microbe-based product of the subject invention is simply the fermentation broth containing the microorganism and/or the microbial metabolites produced by the microorganism and/or any residual nutrients. The product of fermentation may be used directly without extraction or purification.

However, extraction and purification can be easily achieved using standard extraction and/or purification methods or techniques described in the literature. For example, in certain embodiments, the microbe-based product comprises simply the by-products of microbial growth, either in crude or purified form. In particular embodiments, the by-products are biosurfactants produced by the microorganisms grown according to the subject invention.

The microbes and/or broth resulting from the microbial growth can be removed from the growth vessel and transferred via, for example, piping for immediate use.

In other embodiments, the composition (microbes, broth, or microbes and broth) can be placed in containers of appropriate size, taking into consideration, for example, the intended use, the contemplated method of application, the size of the fermentation tank, and any mode of transportation from microbe growth facility to the location of use. Thus, the containers into which the microbe-based composition is placed may be, for example, from 1 gallon to 1,000 gallons or more. In other embodiments the containers are 2 gallons, 5 gallons, 25 gallons, or larger.

In certain embodiments, the compositions of the subject invention have advantages over, for example, biosurfactants alone, including one or more of the following: high concentrations of mannoprotein as a part of yeast cell wall's outer surface (mannoprotein is a highly effective bioemulsifier capable of reaching up to an 80% emulsification index); the presence of biopolymer beta-glucan (an emulsifier) in yeast cell walls; the presence of biosurfactants in the culture, which are capable of reducing both surface and interfacial tension; and the presence of metabolites (e.g., lactic acid, ethanol, etc.).

Upon harvesting the microbe-based composition from the growth vessels, further components can be added as the harvested product is placed into containers and/or piped (or otherwise transported for use). The additives can be, for example, buffers, carriers, other microbe-based compositions produced at the same or different facility, viscosity modifiers, preservatives, nutrients for microbe growth, tracking agents, solvents, biocides, other microbes and other ingredients specific for an intended use.

Other suitable additives, which may be contained in the formulations according to the invention, include substances that are customarily used for such preparations. Example of such additives include surfactants, emulsifying agents, lubricants, buffering agents, solubility controlling agents, pH adjusting agents, preservatives, stabilizers and ultra-violet light resistant agents.

In one embodiment, the composition may further comprise buffering agents including organic and amino acids or their salts. Suitable buffers include citrate, gluconate, tartarate, malate, acetate, lactate, oxalate, aspartate, malonate, glucoheptonate, pyruvate, galactarate, glucarate, tartronate, glutamate, glycine, lysine, glutamine, methionine, cysteine, arginine and a mixture thereof. Phosphoric and phosphorous acids or their salts may also be used. Synthetic buffers are suitable to be used but it is preferable to use natural buffers such as organic and amino acids or their salts listed above.

In a further embodiment, pH adjusting agents include potassium hydroxide, ammonium hydroxide, potassium carbonate or bicarbonate, hydrochloric acid, nitric acid, sulfuric acid or a mixture thereof In one embodiment, additional components such as an aqueous preparation of a salt as polyprotic acid such as sodium bicarbonate or carbonate, sodium sulfate, sodium phosphate, sodium biphosphate, can be included in the formulation.

Advantageously, in accordance with the subject invention, the microbe-based product may comprise broth in which the microbes were grown. The product may be, for example, at least, by weight, 1%, 5%, 10%, 25%, 50%, 75%, or 100% broth. The amount of biomass in the product, by weight, may be, for example, anywhere from 0% to 100% inclusive of all percentages therebetween.

Optionally, the product can be stored prior to use. The storage time is preferably short. Thus, the storage time may be less than 60 days, 45 days, 30 days, 20 days, 15 days, 10 days, 7 days, 5 days, 3 days, 2 days, 1 day, or 12 hours. In a preferred embodiment, if live cells are present in the product, the product is stored at a cool temperature such as, for example, less than 20° C., 15° C., 10° C., or 5° C. On the other hand, a biosurfactant composition can typically be stored at ambient temperatures.

EXAMPLES

A greater understanding of the present invention and of its many advantages may be had from the following examples, given by way of illustration. The following examples are illustrative of some of the methods, applications, embodiments and variants of the present invention. They are not to be considered as limiting the invention. Numerous changes and modifications can be made with respect to the invention.

Example 1—Cultivation of *Pichia* Species for Use in Production of Personal Care Compositions

*Pichia* yeasts can be used to produce a variety of personal care compositions, as their cell derivatives can eliminate fungus that contaminates the skin, reduce pathogenic yeasts growing on the skin and mucosal surfaces, decrease bacterial contamination of the skin and mucosa, and stimulate the production of collagen and elastin in skin cells (to name a few).

The basic cultivation medium for producing *Pichia anomala* (*Wickerhamomyces anomalus*), *Pichia kudriavzevii* and *Pichia guilliermondii* (*Meyerozyma guilliermondii*) is identical for all three species. The medium comprises 2% glucose, 1% yeast extract, 1% canola oil, 5% glycerol, and 50 mM citrate buffer. If *Pichia guilliermondii* is being cultivated for production of chitinase, 0.1% micronized chitin is added. If organic status is desired for the cosmetic product, no inorganic salts are used, and all nutrient medium components must be certified for the organic status.

The temperature for fermentation can range from 25-30° C., and initial pH can range from 5.5-6.0. Saturated oxygen can range from 15-25% (of 100% ambient air). Total fermentation time can be up to 72 hours (determined by reaching the stationary phase).

Once a culture has been produced, it should immediately be cooled down to 5-10° C. to prevent possible degradation of active substances in the supernatant. Then the yeast biomass and yeast supernatant are isolated via centrifugation or microfiltration (or combination thereof) through a 0.1-micron filter while keeping the process at a temperature no higher than 10° C.

Protein molecules can be precipitated using a salting technique. The proteins are salted out by increasing concentration of salt, i.e., ammonium sulfate. After the proteins are concentrated 10-20 folds (or more, depending on the necessary concentration for the final personal care product), they are collected and washed out by a cold saline solution 2-3 times (with constant mixing for 1 hour each time).

Enzymatic activity of the concentrated product can be stabilized by mixing it with sodium alginate to a final concentration of 1% sodium alginate, or mixing it with xanthan gum to a final concentration of 0.5% of xanthan gum.

The antibacterial or antifungal activity of the final resulting substrate can be tested. Antifungal capabilities can be tested by well plate assays with *Candida* yeasts (of clinical significance) and *Malassezia* fungus, whereas for antibacterial activity, the cultures of *E. coli* and *P. aeruginosa* can be used. Growth inhibition should be measured using the diameter of inhibition in millimeters around the well.

Once testing has been conducted, the resulting composition can be used to produce a variety of personal care products, including cosmetic ointments, creams, shampoos, soaps, bath salts, sanitizing solutions and oils for hands and feet, facial washes and creams, and others.

The yeast biomass resulting from these cultivation methods can be used for preparation of other products, including animal and fish feed as a source of proteins, phytase, vitamins and minerals, as well as any other application where live or inactive yeast cells are useful, e.g., soil amendments for agriculture and horticulture, and enhanced oil recovery in oil drilling operations.

Example 2—Fermentation of Starmerella Bombicola for Sophorolipid (SLP) Production in a 550 Gallon Reactor A portable, fully enclosed reactor, designed specifically for yeast growth and biosurfactant production, is operated by PLC and comprises water filtration, a temperature control unit, an impeller and a microsparger. The reactor has a working volume of 500 gallons when growing *S. bombicola* for SLP production.

In preferred embodiments, the nutrients for SLP production comprise glucose, urea, yeast extract, and used vegetable cooking oil.

The reactor is inoculated with 50 liters of liquid culture grown in another reactor. The duration of the cultivation cycle for SLP production is 5 days, at 25° C. and pH 3.5. The final concentration of SLP is roughly 10-15% of working volume, containing 70-75 gallons of SLP.

The culture can be collected into a separate tank. After SLP is allowed to settle to the bottom of the tank, it can be removed and processed as desired. The remaining (approximately) 420 gallons of culture in the tank can comprise from 3-5 g/L of residual SLP.

Example 3—Methods of Treating a Skin Condition

In one embodiment, the subject invention provides methods of treating a skin condition, wherein the topical cosmetic composition is applied directly to an area of the skin, i.e., integument, where such a condition exists. The composition can be applied, for example, to the skin of the face, ears, scalp, neck, back shoulders, arms, hands, chest, stomach, underarms, feet, buttocks, and legs.

In some embodiments, "applying" the composition can comprise spreading the composition on the area of skin and leaving the composition on, and/or rubbing it into, the skin until it is fully absorbed. In some embodiments, the composition can be applied to the skin for a certain amount of time and then rinsed from the skin using, for example, water.

In certain embodiments, the topical cosmetic composition is applied every other day, once daily, or twice daily. In some embodiments, the topical composition is applied every other day, once daily, or twice daily, for an indefinite period of time, e.g., for at least one, two, three weeks, or longer, in order to achieve and/or maintain the treatment of the skin condition.

In one embodiment, the composition can be applied to the skin in an amount from about 0.001 to about 100 mg per $cm^2$ of skin, more typically from about 0.01 to about 20 $mg/cm^2$, or from about 0.1 to about 10 $mg/cm^2$. More or less may be used, however, depending upon the size of the area of skin to be treated.

In preferred embodiments, the composition comprises one or more biosurfactants selected from glycolipids (e.g., SLPs, MELs, TLs and RLPs) and lipopeptides (e.g., surfactin, iturin and fengycin). In additional embodiments, the composition preferably comprises therapeutically effective amounts of enzymes and/or proteins produced by microorganisms, such as, e.g., exo-beta-1,3-glucanase, chitinase, esterases, lipases, glycosidases, amylases, and proteases beneficial for improving skin health.

Other ingredients that are helpful for improving skin health can be applied with the composition, depending upon the skin condition being treated.

The topical cosmetic compositions and methods of the subject invention can be used to treat and/or prevent a variety of skin conditions, including, for example, age spots (e.g., hyperpigmentation), acne, scars, body odor, aging-related conditions (e.g., wrinkles, looseness and dryness), and scalp issues (e.g., dandruff, seborrheic dermatitis and hair loss). Additionally, the topical cosmetic compositions can be used as a cleanser to remove makeup and other impurities from the face and skin. The method can be applied according to any of the following Examples, though it is not intended to be limited thereto.

Example 4—Hyperpigmentation Conditions

In some embodiments, a method is provided for treating age spots or other hyperpigmentation conditions on a subject's skin, wherein the topical composition is applied directly to an area of the skin where such a condition exists for a time sufficient to achieve a desired reduction of pigmentation. In preferred embodiments, the topical cosmetic composition comprises a combination of MELs and SLPs. In one embodiment, the composition is formulated as a lotion, gel or cream.

In certain embodiments, the composition is applied at least once or twice daily for at least one, two, three weeks, or longer. In some embodiments, the topical composition is applied daily for an indefinite period of time in order to achieve and/or maintain a level of reduction in pigmentation of the skin.

In certain embodiments, the subject invention provides methods of treating actinic keratoses, seborrheic keratoses, and other hyperpigmentation conditions of the skin, including treating, ameliorating, diminishing the appearance of, or preventing such conditions, by applying a topical cosmetic composition of the subject invention to the skin in need of treatment.

In some embodiments, the method is also useful for reducing otherwise unwanted pigmentation, such as by lightening the skin overall, as well as by improving the signs of environmental, age-related, or UV-related skin aging.

As used herein, "hyperpigmentation condition" refers to any condition or disorder of the skin wherein discoloration or an abnormally colored growth on the skin occurs. Hyperpigmentation can include excessive or unwanted pigmentation. The hyperpigmentation may result from increased presence of one or more of the different types of melanin biosynthesized in skin and/or follicles and deposited in hair or skin, relative to a subject's baseline pigmentation. Factors such as aging, environmental stress, and UV exposure can be potential causes of the development of hyperpigmentation. Examples of hyperpigmentation conditions include, but are not limited to, age spots, liver spots, freckles, mottled and discrete pigmentation, melasma and the like.

Treatment of hyperpigmentation or hyperpigmented skin or hair refers to eradicating, reducing, ameliorating, reversing or preventing one or more of the unwanted features associated with hyperpigmentation, such as producing a perceptible lightening of the skin or hair in the affected area. Lightening hyperpigmented areas of the skin may be desirable, in one embodiment, in diminishing age spots; lightening a suntan; evening or optimizing skin tones, e.g., in areas of mottled hyperpigmentation; in treating melasmic and chloasmic patches, freckles, and post-injury hyperpigmentation.

In some embodiments of the subject methods, the compositions are applied directly to a site of hyperpigmentation on the skin (i.e., directly onto an age spot). In some embodiments, the compositions are applied daily to achieve and/or maintain a reduction in pigmentation in the skin.

The topical composition may remain on the affected area in need of lightening or may be rinsed off or otherwise removed, depending on the mode of application.

In certain embodiments, application of the topical cosmetic composition may be repeated for a time sufficient to achieve a reduction in pigmentation in the area of application. In order to maintain the desired effect, the method can be continued for as long as the effect is desired. This may entail topical application at least once daily for at least one week, at least two weeks, at least four weeks, or at least eight weeks or more. Once the application of the topical composition is discontinued, the desired reduction in pigmentation may also diminish.

The method may be employed prophylactically to forestall the development of hyperpigmentation conditions on the skin.

In some embodiments, the compositions and methods are useful for lightening skin, which includes eradicating, reducing, ameliorating, and/or reversing a baseline degree of subject pigmentation. Skin lightening may be measured by observing changes in Fitzpatrick scale value of a subject. The Fitzpatrick Scale, Fitzpatrick skin typing test, or Fitzpatrick phototyping scale, is a numerical classification schema for the color of skin, and remains a recognized tool for dermatologic research of skin color.

The Fitzpatrick Scale measures several components, including Genetic Disposition, Reaction to Sun Exposure and Tanning Habits, and classifies skin into six types: Type I (scores 0-7) refers to white, very fair skin, freckles, typical albino skin, that always burns, never tans; Type II (scores 8-16) refers to white, fair skin, that usually burns, or tans with difficulty; Type III (scores 17-24) refers to beige, which is very common, and which sometimes suffers mild burn, gradually tans to a light brown; Type IV (scores 25-30) refers to beige skin with a brown tint, which is typical of Mediterranean Caucasian skin, and which rarely burns, tans with ease to a moderate brown; Type V (scores over 30) refers to dark brown skin which very rarely burns, tans very easily; Type VI refers to black skin that never burns, tans very easily, and is deeply pigmented.

In some embodiments of the invention, the treatments are capable of changing the treated area of skin by at least one or two skin types on the Fitzpatrick scale. When lightening skin, it may be desirable to apply the composition over a large area of skin (e.g., over the entire skin of the face).

Skin for which the subject composition may be useful includes, but is not limited to, discolored or uneven skin, dark complexions, hyperpigmented skin, post-injury hyperpigmented skin, dark circles under the eyes, post-inflammation hyperpigmented skin, skin having age spots, liver spots, melasma, cholasma or freckles, yellowed skin, stained nails, or skin, scalp, legs, face, or other areas where lightening or color reduction are desired.

Specific benefits which may be achieved include, but are not limited to, reducing pigmentation of dark or hyperpigmented skin; reducing age spots or liver spots; reducing pigmented birthmarks, sun damage, tans, and pigmented acne marks; evening out or optimizing skin discoloration; decreasing the appearance of dark circles under the eyes; treating melasma, cholasma, freckles, yellowing of skin, and post-inflammation and post-injury hyperpigmentation; lightening hair on the scalp, legs, face, and other areas where whitening and color reduction are desired; and removing or reducing nail stains.

Example 5—Actinic Keratosis (Using 1% SLP Water and Cream Solutions)

A water solution of 1% by weight SLP was tested on a flat brown spot on a human subject's face. Initially, the spot had two large sub-spots near the right eye, each the size of a dime. After two months of daily application of the solution, the upper sub-spot nearly disappeared and the lower sub-spot became significantly lighter.

A cream composition containing 1% by weight SLP was prepared by mixing SLP with a commercial moisturizing cream. Treatment was conducted by applying the cream on three actinic keratosis spots. The cream was applied twice a day. One of the spots, which began gibbous, became flatter and lighter in color. Another spot, which began flat, became lighter and divided into two spots, with a light skin color in between. The third spot lightened to a light shade of brown.

Example 6—Acne Vulgaris

In certain embodiments, the subject compositions and methods can be used for treating a skin condition selected from acne and/or other blemish-causing conditions. The treatment of acne can comprise preventing, removing and/or reducing the appearance of acne and/or other blemishes of the skin.

In one embodiment, the method of treating acne comprises applying a topical cosmetic composition of the subject invention to a subject's skin, wherein the topical cosmetic composition comprises MELs, SLPs or a combination thereof. In one embodiment, the MELs are added to the composition in an amount of about 0.5% to 2.0% by weight, preferably about 1.0%. In one embodiment, the SLPs are added in an amount of about 0.1% to 1% by weight, preferably about 0.5%.

In one embodiment, the composition is formulated as a gel, lotion or cream. In another embodiment, the composition is formulated as a cleanser or soap.

The method of treating acne can further comprise applying a therapeutically effective amounts of a known comedolytic or anti-acne agent. For example, from about 0.001% to about 5.0% by weight of hydroxy acid, glycolic acid, lactic acid, salicylic acid, retinoids, benzoyl peroxide, erythromycin, tretinoin, tazarotene, azelaic acid, adapalene, dapsone, and clindamycin can be applied. The salt forms of these compounds may also be utilized.

Symptoms of acne or acne-like conditions include, but are not limited to, the appearance of various types of skin blemishes (e.g., lesions, comedones, macules, whiteheads, blackheads, pustules, papules, nodules and cysts), which can cause symptoms such as inflammation, pain, redness, swelling, bumps, scarring, scabbing and infections.

The term "lesion" is generally used to denote an infected or diseased patch of skin. A lesion can involve an infected sebaceous gland. Some lesions are more severe than others. Examples of skin lesions are comedones, macules, papules, pustules, nodules and cysts. The term "comedo" (plural "comedones") is used to describe a sebaceous follicle plugged with dirt, other cells, tiny hairs, or bacteria. Comedones include the so-called "blackheads," which can also be referred to as "open comedones," which have a spot or a surface that appears black. Comedones also include slightly inflamed, skin colored bumps, as well as "whiteheads," which have a spot or a surface that appears white. The term "macule" generally refers to a flat spot or area of the skin with a changed color, such as a red spot. The term "pustule" is generally used to refer to an inflamed, pus-filled lesion, or a small inflamed elevation of the skin that is filled with pus. The term "papule" is generally used to refer to a small, solid, usually inflammatory elevation of the skin that does not contain pus. The term "nodule" is generally used to refer to an elevation of a skin that is similar to a papule but is white and dome-shaped. Colloquially, a papule, a pustule or a nodule can be referred to as a "pimple" or a "zit." The term "cyst" generally refers to an abnormal membranous sac containing a liquid or semi-liquid substance containing white blood cells, dead cells, and bacteria. Cysts can be painful and extend to deeper layers of skin.

Depending on severity, acne can be mild, moderate or severe. Mild acne is generally categorized by the appearance of blackheads and whiteheads, but can also include papules and pustules. Moderate acne is generally characterized by appearance of more painful, deep-rooted, inflamed lesions, which can result in scarring. Severe acne is characterized by the appearance of deep-rooted inflammatory lesions, including cysts and nodules, which can be painful and can produce scarring. Acne conglobata is a category of acne characterized by highly inflammatory cysts that communicate under the skin with abscesses and burrowing sinus tracts.

Specifically, treatment of acne or its related symptoms refers to eradicating, reducing, ameliorating, reversing or preventing one or more of the unwanted features associated with acne, such as reducing the redness, pain, inflammation and overall appearance of comedones in the affected area. Treatment of acne can also lead to lessening the severity of acne in a patient.

The subject compositions and methods can be used to treat blemishes caused by mild, moderate, severe and cystic acne. In one embodiment, the method comprises applying the composition at least once or twice daily for at least one, two, three weeks or longer. The composition can be applied daily for an indefinite period of time in order to achieve and/or maintain a reduction of blemishes and related symptoms.

Example 7—Skin Replenishment

In certain embodiments, the subject compositions and methods can be used for replenishing skin. In one embodiment, a method is provided for replenishing skin in need thereof, by applying a topical cosmetic composition of the subject invention to the skin, wherein the composition comprises MELs. In preferred embodiments, the amount of MELs in the composition is about 0.5% to 2.0% by weight, preferably about 1.0%. The composition can be formulated as, for example, a gel, lotion or cream.

As used herein, skin in need of replenishment is skin that is afflicted with a skin condition selected from dryness, roughness, fragility, looseness, lack of suppleness, dullness, wrinkles, any aging-related skin condition or any skin condition caused by environmental factors, such as, e.g., sun, wind, heat, cold, makeup, oil, dirt or pollution.

In one embodiment, the method of replenishing skin further comprises applying a therapeutically effective amount of a known skin-replenishing compound. For example, from about 0.001 to about 5.0% by weight of hyaluronic acid, ceramides, sodium PCA, glycerin, glycerol, cholesterol and/or phospholipids can be added, as well as silicones, petrolatum, triglycerides, omega fatty acids, AHAs (e.g., glycolic acid) and/or BHA (e.g., salicylic acid).

In one embodiment, the method of replenishing skin can further comprise applying the protein lactoferrin to the skin.

The method may be employed prophylactically to forestall aging of skin, including in individuals that have not manifested signs of skin aging, for example, in individuals under 25 years of age. The method may also reverse or treat signs of aging once manifested as is common in individuals over 25 years of age, or to slow the progression of dermatological aging in such individuals.

Example 8—Scalp and Hair Health

In certain embodiments, the subject compositions and methods can be used for treating a scalp condition or hair condition. In one embodiment, a method is provided for treating a scalp and/or hair condition by applying a topical cosmetic composition of the subject invention to the scalp and/or the hair, wherein the composition comprises MELs and acidic-form SLPs. In one embodiment, the amount of MELs in the composition is about 0.1% to about 1.0% by weight, preferably about 0.2%. In one embodiment, the amount of acidic-form SLPs in the composition is about 0.01% to 1.0%, preferably about 0.1%.

As used herein, the terms "scalp condition" and "hair condition" encompass human and animal conditions, disorders, or diseases affecting the scalp and/or the hair. Such conditions include, but are not limited to, dry hair or scalp, thinning hair, brittle hair, hair loss, male pattern baldness, alopecia, ringworm, seborrheic eczema, seborrheic dermatitis, cradle cap, acne, psoriasis, head lice, tricorrhexis nodosa, dandruff, for example, caused by Malassezia fungi, folliculitis caused by, for example, Staphylococcus aureus, and others.

In one embodiment, the topical cosmetic composition is formulated as a shampoo, conditioner, mousse, hair gel, or hair lotion. In one embodiment, the composition can further comprise certain additives, including, for example, proteins (e.g., hydrolyzed vegetable protein, hydrolyzed wheat protein, hydrolyzed milk protein, hydrolyzed silk and hydrolyzed collagen), vitamins (e.g., panthenol, biotin, vitamin E acetate, vitamin A and D palmitate), moisturizers/humectants (e.g., glycerin, propylene glycol, sodium PCA, amino acid-based surfactants, and HLA), emollients (e.g., esters, isopropyl myristate, decyl oleate, C12-15 alkyl benzoate), oils (e.g., coconut, jojoba, aloe vera, safflower, almond, argon), botanicals (e.g., chamomile, aloe, rosemary), and perfumes (e.g., lavendar, ylang ylang, patchouli), as well as preservatives, dyes, pH adjusters and chelating agents.

The method can comprise applying about 10 ml, or 2 teaspoons to 2 tablespoons of the composition to the scalp and/or hair (for example, by rubbing and/or lathering the composition thereon), allowing the composition to sit for 1 minute to 5 minutes, and then rinsing the composition with water. In one embodiment, the composition is rubbed and/or lathered into the scalp and/or hair without rinsing. The amount of composition applied to the scalp and/or hair can depend on the length, amount and thickness of the subject's hair.

Example 9—Body Odor

In certain embodiments, the subject compositions and methods can be used for treating body odor.

Body odor is typically caused by the presence of Gram-positive *Propionibacteria* and *Staphylococcus epidermis*, which live in the ducts of the sebaceous glands and produce propionic acid and isovaleric acid. These compounds can produce undesirable odors.

In one embodiment, a method is provided for treating body odor by applying a topical cosmetic composition of the subject invention to the source of the body odor, for example, the skin of the underarms. The topical cosmetic composition can comprise MELs and SLPs. In one embodiment, the amount of MELs in the composition can be from about 0.01% to about 1.0% by weight, preferably about 0.1%. In one embodiment, the amount of SLPs in the composition can be from about 0.01% to about 1.0% by weight, preferably about 0.1%.

In one embodiment, the composition is formulated as a liquid, a stick, a gel, a spray or a wipe.

The composition can further be applied with, for example, carriers (e.g., propylene glycol, dipropylene glycol and water), gelling agents (e.g., sodium stearate, sodium palmitate, sodium arachidate, sodium behenate), clarifying agents (e.g., nonionic surfactants), fragrances, chelating agents (e.g., disodium or tetrasodium EDTA), pH adjusters (e.g., aminomethyl propanol, poloxamine, sodium hydroxide), antioxidants (e.g., BHT) and colorants (e.g., water and/or alcohol soluble dyes).

Example 10—Scar Reduction

In certain embodiments, the subject compositions and methods can be used for reducing the appearance of dermal scars, for example, scars resulting from injury, acne, or surgery, including plastic/reconstructive surgery. Scars often result from the overproduction of collagen by modified dermal fibroblasts, or myofibroblasts. In normal skin, fibroblasts produce collagen fibers, which align to form a random "basketweave" pattern.

In response to a wound, fibroblasts may be transformed by inflammatory stimulants into myofibroblasts. Myofibroblasts deposit collagen in cross-linked patterns, wherein the collagen fibers align in a single direction parallel to the skin. In addition, there is greater collagen density and larger fiber size in scars compared to normal tissue. The abundant myofibroblasts fail to undergo apoptosis, and continue to circulate the collagen matrix, produce new collagen, and cause the new skin to stiffen and contract.

In one embodiment, a method is provided for reducing the appearance of a scar by applying a topical cosmetic composition of the subject invention to the scar, wherein the composition comprises MELs and SLPs, and/or other agents for skin health. In one embodiment, the composition can be formulated as a gel or a cream. In preferred embodiments, the composition further comprises Aloe vera extract, for example, in gel form.

In one embodiment the amount of MELs in the composition is from about 0.1% to 2.0% by weight, preferably about 1.0%. In one embodiment, the amount of SLPs in the composition is from about 0.01% to about 1.0% by weight, preferably about 0.5%.

Advantageously, in one embodiment, the subject compositions can help to dissolve the misaligned collagen matrix that forms a dermal scar, as well as inhibit the number of myofibroblasts present in the dermis in order to diminish the appearance of the scar.

We claim:

1. A method for treating a skin condition, wherein the method comprises applying a topical composition to human skin having said skin condition, wherein:

said skin condition is acne; and the topical composition comprises a broth resulting from cultivation of a *Bacillus amyloliquefaciens* bacterium, and further comprising a mannosylerythritol lipid and a sophorolipid, wherein the composition is applied to skin in an amount from about 0.1 to about 10 mg/cm$^2$, or the composition comprises the sophorolipid in an amount of about 0.1% to 1% by weight and the mannosylerythritol lipid in an amount of about 0.5% to 2.0% by weight.

2. The method of claim 1, wherein the topical composition further comprises resveratrol, hyaluronic acid and/or polyacrylic acid.

3. The method of claim 1, wherein the topical composition is formulated as a liquid, cream, gel, ointment, lotion, or spray.

4. The method of claim 1, wherein the topical composition is formulated as a cream.

* * * * *